United States Patent [19]

Mitsuhashi et al.

[11] Patent Number: 4,758,549

[45] Date of Patent: Jul. 19, 1988

[54] LYMPHOKINE, MONOCLONAL ANTIBODY SPECIFIC TO THE LYMPHOKINE AND THEIR PRODUCTION AND USES

[75] Inventors: Masakazu Mitsuhashi; Masashi Kurimoto, both of Okayama, Japan

[73] Assignee: Kabushiki Kaisha Mayashibara Seibutsu Kagaku Kenkyujo, Japan

[21] Appl. No.: 675,291

[22] Filed: Nov. 27, 1984

[30] Foreign Application Priority Data

Dec. 13, 1983 [JP] Japan ............................ 58-233570
Dec. 27, 1983 [JP] Japan ............................ 58-24598

[51] Int. Cl.$^4$ .................... A61K 37/00; C07K 15/14; C12P 21/00; C12N 15/00
[52] U.S. Cl. ......................... 514/8; 530/351; 435/68; 435/172.2
[58] Field of Search ............ 530/351, 395; 424/88; 435/68, 240; 514/8

[56] References Cited

U.S. PATENT DOCUMENTS

| 4,438,032 | 3/1984 | Golde et al. | 435/68 |
| 4,481,137 | 11/1984 | Ohneshi et al. | 435/68 |
| 4,495,282 | 1/1985 | Ohneshi et al. | 435/68 |

FOREIGN PATENT DOCUMENTS 2168355 5/1986 United Kingdom .

*Primary Examiner*—Blondel Hazel
*Attorney, Agent, or Firm*—Browdy and Neimark

[57] ABSTRACT

Disclosed is an invention relating to a novel lymphokine and to the production and uses thereof. The invention also relates to a monoclonal antibody specific to the lymphokine and its production. The novel lymphokine is a glycoprotein having a molecular weight of 20,000±2,000 daltons; isoelectric point pI, 5.6±0.2; electrophoretic mobility Rf, 0.29±0.02; and cytotoxic on a mouse cell line L 929. The lymphokine inhibits significantly the growth of malignant human tumors in vivo. The monoclonal antibody is IgM or IgG class, and neutralizes specifically the cytotoxic activity of the lymphokine.

7 Claims, No Drawings

LYMPHOKINE, MONOCLONAL ANTIBODY SPECIFIC TO THE LYMPHOKINE AND THEIR PRODUCTION AND USES

FIELD OF THE INVENTION

The present invention relates to a novel lymphokine, as well as to their production and uses. It also relates to a monoclonal antibody specific to the lymphokine and its production.

BACKGROUND OF THE INVENTION

Lymphotoxin (LT) and tumor necrosis factor (TNF) are known as lymphokines which damage tumor cells. For example, LT is described in Aoki, Ryuichi et al., *SHIN-MENEKIGAKU SOSHO*, Vol. 6, "Lymphokine", pp. 87–105 (1979), published by Igaku-Shoin, Tokyo, *In Vitro Method in Cell-Mediated Immunity*, edited by Bloom, B. R. & Glade, P. R., published by Academic Press, Inc. (1971), and *Cellular Immunology*, Vol. 38, pp. 388–402 (1978); and TNF is described in Carswell, E. A. et al., *Proc. Nat. Acad. Sci. USA*, Vol. 72, No. 9, pp. 3,666–3,670 (1975), and *Lymphokines*, Vol. 2, pp. 235–272, "Tumor Necrosis Factor", edited by Pick, E., published by Academic Press, Inc. (1981). Ohnishi, H. et al. discloses a lymphokine glycoprotein in Japan Patent Kokai No. 146,293/83.

Milstein, C. reviews the details of monoclonal antibodies in *Scientific American*, Vol. 243, No. 4, pp. 56–64 (1980).

DETAILED DESCRIPTION OF THE INVENTION

The present inventors have studied lumphokines over a period of years. Eventually, we discovered a novel lymphokine having physicochemical properties entirely different from those of known lymphokines, and its cytotoxic activity on malignant tumor cells. Thus, we established the production and uses of such lumphokine, as well as a monoclonal antibody specific to such lumphokine and its production. This is the present invention.

More particularly, the present invention relates to a novel human lumphokine having the following physicochemical properties:
(a) Molecular weight;
    20,000±2,000 daltons
(b) Isoelectric point;
    pI=5.6±0.2
(c) Electrophoretic mobility;
    on Disc-PAGE, Rf=0.29±0.02
(d) uv-Absorption spectrum;
    an absorption maximum at a neighborhood of 280 nm
(e) Solubility in solvents;
    soluble in water, physiological saline and phosphate buffer
    scarcely soluble or insoluble in ethyl ether, ethyl acetate or chloroform
(f) Coloring reaction;
    protein-positive by the Lowry's method or microburet method
    sugar-positive by the phenol-sulfonic acid method or anthrone-sulfuric acid method
(g) Biological activities;
    cytotoxic on L 929 cell
    growth-inhibitive on KB cell
    substantially free from interferon activity
(h) Stability in aqueous solution;
    stable up to 60° C. when incubated at pH 7.2 for 30 minutes
    stable in the pH range of 4.0–11.0 when incubated at 4° C. for 16 hours, and
(i) Stability on cryopreservation;
    stable at −10° C. over a period of one month or longer,
and their production and uses. Also, it relates to a monoclonal antibody specific to the noval lymphokine and its production.

The novel lymphokine will be abbreviated simply as "LK 1" hereinafter.

LK 1 is produced by exposing an LK 1 producing human cell, e.g. human leukocyte, human lumphocyte and established cell lines thereof, to an LK 1 inducer. Both human leukocyte and lumphocyte can be isolated from fresh human blood. The established human cell line may be proliferated according to conventional in vitro procedure, prior to its use.

For a more efficient practice of the present invention, preferably, an in vitro cell proliferation wherein such human cell line is transplanted directly to a non-human warm-blooded animal, or, alternatively, inoculated in a conventional-type diffusion chamber by which the nutrient body fluid of a non-human warm-blooded animal is supplied to the cell line, is carried out: Unlike in vitro cell proliferation, the in vitro procedure, in addition to obtaining a much higher-tiltered LK 1 with the proliferated human cell, requires no or much less nutrient medium containing expensive serum and less cares during the cell proliferation. More particularly, in the in vivo procedure using a non-human warm-blooded animal as the host, the human cell line can be proliferated easily while utilizing the nutrient body fluid supplied from a non-human warm-blooded animal by transplanting the cell line to a non-human warm-blooded animal, or, alternatively, placing the cell line in a conventional-type diffusion chamber devised to receive the body fluid, and embedding or placing the chamber in or on the animal. In each case, the animals are fed in usual way. Furthermore, the in vivo procedure is characterized by additional features that a much more stabilized and rapid cell proliferation, a higher cell production, and an extremely higher LK 1 production per cell are attainable than with the in vivo procedure.

The human cell lines usable in the invention may be those which are LK 1-producible, transplantable to a non-human warm-blooded animal, and readily proliferatable therein. For example, a variety of human cell lines listed in *Protein, Nucleic Acid and Enzyme*, Vol. 20, No. 6, pp. 616–643 (1975) are feasible in the invention. Especially suitable are human lymphoblastoid lines, such as Namalwa (ATCC CRL 1432), as described in *Journal of Clinical Microbiology*, Vol. 1, pp. 116–117 (1975); BALL-1, TALL-1 and NALL-1, as described by Miyoshi, I., *Nature*, Vol. 267, pp. 843–844 (1977); M-7002 and B-7101, as described in *The Journal of Immunology*, Vol. 113, pp. 1,334–1,345 (1974); JBL, EBV-Sa, EBV-Wa, MOLT-3 (ATCC CRL 1552) and EBV-HO, as described in *The Tissue Culture*, Vol. 6, No. 13, pp. 527–546 (1980); CCRF-SB (ATCC CCL 120); CCRF-CEM (ATCC CCL 119); BALM-2; DND-41; and other established cell lines obtained by transforming normal monocyte or granulocyte with any circinogenic virus, agent, or radiation.

The proliferation rate and/or LK 1 productivity per cell of these cell lines may be improved by treating them by means of cell fusion using polyethylene glycol or Sendai virus, or by gene recombinant technique using nuclease enzyme, ligase enzyme, DNA polymerase enzyme, etc. The listing of such employable human cell lines in the SPECIFICATION will be intended in no way to limit the scope of the invention.

Dependent upon the case, one or more members of these cell lines may be used in combination in the steps up to the LK 1 induction which will be described hereinafter. Also, human leukocyte or lumphocyte, prepared, e.g. from fresh human blood, may be used in combination with the cell line(s).

The non-human warm-blooded animal usable in the invention may be one of those wherein such human cell is proliferatable. For example, fowls, such as chicken and pigeon; or mammalians, such as dog, cat, monkey, rabbit, goat, pig, horse, cow, guinea pig, rat, nude rat, hamster, mouse, or nude mouse, are feasible. Since transplantation of the human cell to such animal results in the elicitation of undesirable immunoreaction, the use of a non-human warm-blooded animal in the possible youngest stage, e.g. egg, embryo, or foetus, or newborn or infant animal, is desirable in order to reduce such immunoreaction as much as possible. Prior to the transplantation, the animal may be treated further with x-ray or $\gamma$-ray irradiation, about 200-600 rem, or injection of a suitable antiserum or immunosuppressant in order to reduce the immunoreaction to the possible lowest level. Immunodeficient animals, e.g. nude mouse and nude rate, are suitable as the host animal: Any of the above-mentioned human cell lines can be transplanted in these animals without such pretreatment, and proliferate readily therein with less fear of causing undesirable immunoreaction since they exhibit less immunoreaction even in their adulthood.

One may obtain stabilization of cell proliferation and/or augmentation of LK 1 production by successive transplantation using the same or different non-human warm-blooded animals: For example, these objectives may be attained by first transplanting a human cell line to a hamster and proliferating it therein, then successively transplanting the proliferated human cell to a nude mouse. In this case, the successive transplantation may be carried out with a non-human warm-blooded animal of the same class or order, as well as those of the same species or genus.

The human cell is transplantable in any site of the animal so far as the cell proliferates therein; for example, in allantoic cavity, or intravenously, intraperitoneally, or subcutaneously.

Instead of transplanting the human cell to the animal, any of the above-mentioned human cells can be proliferated with ease by placing it in a conventional-type diffusion chamber of various shapes and sizes, equipped with a suitable means which prevents contamination of the chamber with the animal cell, but supplies the human cell with the nutrient body fluid of the animal, e.g. membrane filter, ultrafilter or hollow fiber of a nominal pore size of about $10^{-7}$-$10^{-5}$ m; embedding, e.g. intraperitoneally, the chamber in the animal; and allowing the human cell to proliferate therein while receiving the nutrient body fluid from the animal. Furthermore, the diffusion chamber can be designed and placed, e.g. on the animal, so that the nutrient fluid in the chamber can circulate freely through the chamber. The culture in the chamber can be observed during the cell proliferation through transparent side window(s), equipped on the chamber wall(s), and/or the chamber per se can be replaced at intervals with a fresh one both to continue the cell proliferation over the period of the life span of the animal without sacrificing and to augment much more the cell production per animal. Since due to the absence of direct contact of the human cell with the animal cell such diffusion chamber elicits much less undesirable immunoreaction, any non-human warm-blooded animal may be readily used without pretreatment to reduce such immunoreaction, and the proliferated viable human cell can be harvested easily therefrom.

Feeding of the animal can be carried out in usual way, and no special care is required even after the transplantation. The period required to obtain maximum cell proliferation is generally within 1-10 weeks. The number of the human cell so obtained may be about $10^7$-$10^{12}$ cells per animal or more. More particularly, according to the invention, the transplanted human cell increase to about $10^2$-$10^7$-fold or more, which is about $10$-$10^6$-fold or higher than that obtained by inoculating and proliferating the human cell on an in vitro nutrient culture medium. This is very favorable in the production of LK 1.

Any method is feasible in the invention as long as LK 1 production can be induced in the proliferated human cell therewith. The proliferated human cell may be exposed in the animal, used as the host for cell proliferation, to an LK 1 inducer. For example, a human cell, proliferated in ascite in suspension, or a tumor cell, formed, e.g. subcutaneously, is directly exposed in vivo to an LK 1 inducer to induce LK 1 production, and the accumulated LK 1 is harvested from the ascite, serum and/or tumor, followed by purification of the LK 1. Alternatively, the proliferated human cell may be harvested from the animal and then exposed in vitro to an LK 1 inducer. For example, the proliferated human cell, obtained by harvesting from ascite suspension, or extracting and disaggregating the tumor mass(es), formed, e.g. subcutaneously, is suspended in a nutrient culture medium, prewarmed to a temperature of about $20°$-$40°$ C., to give a cell density of about $10^5$-$10^8$ cells/ml, and exposed in vitro to an LK 1 inducer, followed by the recovery of the accumulated LK 1 from the culture. When a conventional-type diffusion chamber is used, exposure of the proliferated human cell to an LK 1 inducer is carried out in the chamber or after harvest therefrom.

The human cell so obtained may be cultured in vitro for an additional 1-4 days to regulate its generation time prior to the LK 1 induction.

The LK 1 production per animal may be further augmented by employing one or more of the following methods:

(1) a method wherein the proliferated human cell is exposed to an LK 1 inducer in the animal, which has been used as the host for the cell proliferation, and then harvested from certain site(s) of the animal or its whole body, followed by in vitro exposure of the human cell to an LK 1 inducer.

(2) a method wherein the human cell is repeatedly exposed to an LK 1 inducer, and/or (3) a method wherein the diffusion chamber embedded in or connected to the animal is replaced at intervals with fresh one.

The LK 1 inducer usable in the invention may be a conventional $\alpha$-interferon inducer (IFN-$\alpha$ inducer), such as virus, nucleic acid and nucleotide; or a conventional $\gamma$-interferon inducer (IFN-$\gamma$ inducer), such as, phytohaemagglutinin, concanavalin A, pokeweed mitogen, lipopolysaccharide, endotoxin, polysaccharide, and bacteria. Antigens act as LK 1 inducer on a cell sensitized therewith.

The LK 1 production may be further augmented with a combined use of both IFN-α and IFN-γ inducers as LK 1 inducer. It was confirmed that such combination induces a simultaneous production of human-specific interferon (HuIFN). This is very advantageous in a simultaneous and low-cost mass-production of two or more biologically-active substances, i.e. invaluable LK 1 and HuIFN, as well as in a much more effective utilization of human cells.

The LK 1 so obtained can be recovered by one or more purification and/or separation procedures, e.g. salting-out, dialysis, filtration, centrifugation, concentration, and/or lyophilization. If a much more purified LK 1 preparation is desirable, a preparation of the highest purity can be obtained by the above described procedure(s) in combination with other conventional procedure(s), e.g. adsorption and desorption with ion exchange, gel filtration, isoelectric point fractionation, electrophoresis, ion exchange chromatography, high-performance liquid chromatography, column chromatography, and/or affinity chromatography.

Immobilized monoclonal antibodies obtained by binding a monoclonal anti-LK 1 antibody, which will be described hereinafter, onto a suitable water-insoluble carrier, e.g. BrCN-activated Sepharose, a product of Pharmacia Fine Chemical AB, Uppsala, Sweden, are advantageously usable in a more speedy and easier purification of LK 1.

It was confirmed that the LK 1 thus obtained has the following physicochemical properties:
(a) Molecular weight;
  20,000±2,000 daltons
(b) Isoelectric point;
  pI=5.6±0.2
(c) Electrophoretic mobility;
  on Disc-PAGE, Rf=0.29±0.02
(d) uv-Absorption spectrum;
  an absorption maximum at a neighborhood of 280 nm
(e) Solubility in solvents;
  soluble in water, physiological saline and phosphate buffer
  scarcely soluble or insoluble in ethyl ether, ethyl acetate or chloroform
(f) Coloring reaction;
  protein-positive by the Lowry's method or microburet method
  sugar-positive by the phenol-sulfuric acid method or anthrone-sulfuric acid method
(g) Biological activities;
  cytotoxic on L 929 cell
  growth-inhibitive on KB cell
  substantially free from interferon activity
(h) Stability in aqueous solution;
  stable up to 60° C. when incubated at pH 7.2 for 30 minutes
  stable in the pH range of 4.0-11.0 when incubated at 4° C. for 16 hours, and
(i) Stability on cryopreservation;
  stable at −10° C. over a period of one month or longer.

Also was confirmed that the LK 1 does not effect any substantial cytolysis on normal human cells, but effects a remarkable cytolysis on a variety of human tumor cells as well as on the mouse fibroblastoid line, L 929, to kill these cells. Thus, the LK 1 is favorably usable, e.g. in the form of composition, as prophylactic- and/or therapeutic agent for LK 1-sensitive diseases, e.g. malignant tumors, more particularly, various malignant human tumors, treatment of which has been deemed very difficult.

The process for producing a monoclonal antibody according to the present invention comprises immunizing a non-human warm-blooded animal with the LK thus obtained as the antigen; collecting the antibody-producing cell from the body of the animal; fusing the antibody-producing cell with a myeloma cell; selecting a clone capable of producing an antibody specific to LK 1 from the resultant hybridoma cells; proliferating the clone; and allowing the proliferated cell to produce the monoclonal antibody specific to LK 1.

Such immunization can be obtained by injecting, e.g. intravenously, intraperitoneally or subcutaneously, an aqueous solution, emulsion or suspension of the LK 1 as the antigen into a suitable non-human warm-blooded animal, e.g. chicken, pigeon, dog, cat, monkey, goat, pig, cow, horse, rabbit, guinea pig, rat, hamster or mouse, and feeding the animal for three days or longer to induce antibody production. A conjugate of the LK 1 and a saccharide obtainable according to the teaching of Japan Patent Publication No. 23,847/83 is also feasible as the antigen. The antigen may be injected in single dosage or, if necessary, in two or more dosages at interval(s) of about 3-30 days.

The spleen cell of the immunized animal wherein antibody production has been induced is fused with a myeloma cell of the same or a different species with a suitable procedure, e.g. those reported by Kohler, G. et al. in *Nature*, Vol. 256, pp. 495-497 (1975) and *Eur. J. Immunol.*, Vol. 6, pp. 511-519 (1976). The hybrid cells so obtained are then selected and cloned, after which the clone(s) is cultured in vitro or in vivo, followed by recovery of the accumulated highly-specific monoclonal antibody from the resultant culture. More particularly, the in vivo procedure is more preferable than in vitro procedure because the former procedure attains a much higher proliferation of the clone and a much higher production of the monoclonal antibody without use of expensive serum. In the in vivo procedure, the clone is proliferated while utilizing the nutrient body fluid of a non-human warm-blooded animal of the same or a different species used in the immunization by transplanting the clone to such a non-human warm-blooded animal, or inoculating the clone in a conventional-type diffusion chamber devised to receive the nutrient body fluid of such an animal, and the accumulated monoclonal antibody is recovered from the body fluids such as ascite and blood. Alternatively, after proliferating in vivo, the clone may be cultured on a serum-free culture medium for an additional 1-5 days, followed by recovery of the accumulated monoclonal antibody from the resultant culture.

The monoclonal antibody so obtained can be recovered easily with one or more separation and/or purification procedures, e.g. salting-out, dialysis, filtration, centrifugation, concentration and/or lyophilization. If a much higher purification is desirable, a preparation of the highest purity can be obtained by the above-mentioned procedure(s) in combination with other conventional procedure(s), e.g. adsorption and desorption with ion exchange, gel filtration, isoelectric point fractionation, electrophoresis, ion exchange charmatography, high-performance liquid chromatography, column chromatography, and/or affinity chromatography. The recovery yield of the monoclonal antibody can be improved advantageously by use of an immobilized LK 1 gel obtained by binding a high-purity LK 1 onto a suitable water-insoluble carrier, e.g. BrCN-activated Sepharose.

The monoclonal antibody obtained according to the invention is favorably usable as ligand for affinity chromatography directed to LK 1 production, as well as in diagnosis of a variety of human diseases because of its specificity to LK 1 which has a cytotoxic activity on malignant tumors.

The LK 1 titers were assayed by use of either KB cell or L 929 cell as the target cell: When KB cell was used, the growth inhibition activity on KB cell determined according to the method described in *Cancer Chemotherapy Reports Part 3*, Vol. 3, No. 2, September (1972) with a slight modification; When L 929 cell was used, the cytotoxic activity on L 929 cell in the presence of antinomycin D was determined by the method described in *Lymphokines*, Vol. 2, pp. 245-249, "Tumor Necrosis Factor", edited by Pick, E., published by Academic Press, Inc. (1981) with a slight modification. Throughout the SPECIFICATION, the latter method using L 929 cell was employed unless specified otherwise.

The titers of HuIFN were assayed by the conventional plaque-reduction method using FL cells of human amnion origin described in *Protein, Nucleic Acid and Enzyme*, Vol. 20, No. 6, pp. 616-643 (1975).

The maemagglutination titers were assayed according to the method reported by Salk, S. E., *The Journal of Immunology*, Vol. 49, pp. 87-98 (1944) with a slight modification.

The following Experiments further detail the present invention.

EXPERIMENT A-1

Preparation of partially-purified LK 1

Newborn hamsters were injected with a conventional antiserum prepared from rabbit to weaken their immunoreaction, transplanted subcutaneously with a human lymphoblastoid line, BALL-1, and fed in usual way for three weeks. The tumor masses, formed subcutaneously, were extracted, minced, and disaggregated in physiological saline. The cell suspension so obtained was then washed with RPMI 1640 medium (pH 7.2) supplemented with serum, and resuspended in a fresh preparation of the same culture medium to give a cell density of about $2 \times 10^6$ cells/ml. The cell suspension was added with Sendai virus (about 400 haemagglutination titers/ml), and incubated at 37° C. for 24 hours to induce LK 1 production. The culture was centrifuged at about 4° C. and about $1,000 \times g$, and the resultant precipitant was removed. The supernatant so obtained was dialyzed against physiological saline containing 0.01 M phosphate buffer (pH 7.2) for 20 hours, and treated with a membrane filter. The filtrate was then passed through a column of an immobilized anti-HuIFN antibody, and the unadsorbed fraction was collected. An active fraction was recovered from this fraction by means of chromatofocusing, concentrated, and lyopilized to obtain a powder possessing LK 1 activity.

The specific activity of the powder was about $10^6$ units/mg protein. The LK 1 yield was about $3.0 \times 10^7$ units per hamster.

EXPERIMENT A-2

Preparation of anti-LK 1 antibody

An LK 1 preparation, obtained by the method described in Experiment A-1, was dissolved in physiological saline to give a concentration of about 0.05 w/v % as protein, and the solution was added with the same volume of Freund's complete adjuvant. Mice were immunized by subcutaneously injecting 0.2 ml aliquots of the mixture so obtained, and boosting seven days after the first injection. After inducing anti-LK 1 antibody production in the antibody-producing cell of the animals, the spleens of the animals were extracted, minced, disaggregated, and suspended together with a mouse myeloma cell line, $P_3$-X63-Ag8, purchased from Flow Laboratories, Inc., Rockville, Md. USA, in serum-free Eagle's minimal essential medium (pH 7.2) containing 50 w/v % polyethylene glycol 1000, prewarmed to 37° C. to give respective cell density of $10^4$ cells/ml, followed by 5-minute standing of the resultant mixture. Thereafter, the mixture was diluted 20-times in a fresh preparation of the same culture medium, and the hybridoma cells capable of growing on the hypoxanthine, aminopterin, thymidine containing medium were collected according to the method reported by Davidson, R. L., and Gerald, P. S. in *Somatic Cell Genetics*, Vol. 2, No. 2, pp. 175-176 (1976) to clone the hybridoma cell capable of producing the anti-LK 1 antibody. Mice were transplanted intraperitoneally with the cloned hybridoma cell in a dosage of about $10^6$ cells per mouse, fed for two weeks, and sacrificed. The body fluids of the animals, such as ascite fluid and blood, were recovered, centrifuged, and salted out with ammonium sulfate, followed by the collection of the fractions sedimented at 30-50% saturation. These fractions were dialyzed, and subjected to affinity-chromatography using an immobilized anti-LK 1 antibody gel obtained by reacting an LK 1 specimen, prepared by the method described in Experiment A-1, with BrCN-activated Sepharose at ambient temperature, to obtain an anti-LK 1 antibody fraction which was then dialyzed, concentrated, and lyophilized into powder. This powder exhibited an immunologically-specific neutralization to the cytotoxic activity of LK 1.

The stability of the monoclonal antibody in aqueous solution was studied by assaying the residual neutralizing activities after incubating under prescribed conditions: On incubation at pH 7.2 and different temperatures for 30 minutes, 80% or more of the activity was retained at 60° C., but 90% or more was lost at 70° C. After incubation at 4° C. and different pH levels for 16 hours, the activity was stable in the pH range of 4.0-11.0, but was lost by 90% or more at pH 2.0.

On studying properties of the monoclonal antibody, the present monoclonal antibody was found unresistant to 2-mercaptoethanol, and effected a specific antigen-antibody reaction with anti-mouse immunoglobulin M antibody. Thus, the present monoclonal antibody is grouped into the class of immunoglobulin M antibody.

EXPERIMENT A-3

Preparation and physicochemical properties of highly-purified LK 1

A partially-purified LK 1 specimen, obtained by the method described in Experiment A-1, was subjected to affinity-chromatography using an immobilized monoclonal antibody gel, prepared by the method described in Experiment A-2, to collect LK 1 fractions which were then dialyzed, concentrated and lyophilized.

The resultant was a highly-purified LK 1 preparation having a specific activity of about $10^9$ units/mg protein. The LK 1 assay of the preparation using KB cell gave an approximately the same specific activity.

The physicochemical properties of LK 1 were studied with this preparation.

(1) Molecular weight:

The molecular weight of LK 1 was determined by the electrophoretic methods using SDS-polyacrylamide gel described in Weber, K. and Osborn, M., *J. Biol. Chem.*, Vol. 244, page 4,406 (1969) with a slight modification. Column of 10% acrylamide gel were loaded with about 10 μg aliquots of the preparation in the presence of 0.1% SDS, and charged with 8 mA per column for four hours to effect electrophoresis. After extraction and subsequent LK 1 assay of the active fractions, the molecular weight of LK 1 was 20,000±2,000 daltons.

(2) Isoelectric point:

A 2 hour, 25 W electrofocusing of the preparation using "AMPHOLINE PAGPLATE", a gel product for electrofocusing, commercialized by LKB-Produkter AB, Stockholm, Sweden, gave an isoelectric point pI of 5.6±0.2.

(3) Electrophoretic mobility:

According to the method described in Davis, B. J., *Ann. N.Y. Acad. Sci.*, Vol. 121, page 404 (1964) with a slight modification, about 10 μg aliquots of the preparation were loaded on columns of 10% acrylamide gel, subjected to electrophoresis at pH 8.3 and 3 mA per column for two hours, extracted, and assayed for LK 1 activity to obtain an electrophoretic mobility Rf of 0.29±0.02.

(4) uv-Absorption spectrum:

After analyzing the uv-spectrum of the preparation by use of UV-250 spectrometer, a product of Shimadzu Seisakusho KK, Kyoto, Japan, an absorption maximum was found at a neighborhood of 280 nm.

(5) Solubility in solvent:

Soluble in water, physiological saline and phosphate buffer solution; scarcely soluble or insoluble in ethyl ether, ethyl acetate and chloroform.

(6) Coloring reaction:

Protein-positive by the Lowry's method and the microburet method; sugar-positive by the phenol-sulfuric acid method and ant anthrone-sulfuric acid method.

(7) Biological activity:

A cytotoxic activity on L 929 cell and a growth inhibition activity on KB cell were noted. No substantial HuIFN activity was noted. (8) Stability in an aqueous solution:

(i) Heat stability:

About $1\times10^5$ units/ml aliquots of the preparation were incbated at pH 7.2 and different temperatures for 30 minutes, and the residual cytotoxic activities were assayed. As a result, LK 1 was found stable up to 60° C.

(ii) pH Stability:

0.1 ml aliquots of the preparation ($1\times10^6$ units/ml) were added with 1 ml buffer solution of different pH levels, i.e. McIlvaine buffer at pH 2-7; phosphate buffer, pH 7-8; glycine-NaOH buffer, pH 8-11, and incubated at 4° C. for 16 hours. Thereafter, 0.1 ml of the incubated mixture was adjusted to pH 7.2 with 0.05 M phosphate buffer (pH 7.2), and the residual activity was assayed.

As a result, LK 1 was found stable in the pH range of 4.0-11.0.

(iii) Stability to "DISPASE":

To about $1\times10^5$ units/per ml of the preparation was added "DISPASE", a protease enzyme of Bacillus microorganism, commercialized by Godo Shusei Co., Ltd., Tokyo, Japan, to give an enzyme activity of 100 units/ml, and the mixture was incubated at pH 7.2 and 37° C. for two hours. During the incubation, small portions of the mixture were sampled periodically, and added with calf serum albumin to give a concentration of 1 w/v % to suspend the enzymatic reaction. On assaying the LK 1 activities in the samples, LK 1 was susceptive to DISPASE treatment and lost its activity as the enzymatic reaction proceeded.

(9) Stability to cryopreservation:

The LK 1 preparation was stored in aqueous solution at −10° C. and pH 7.2 for one month, thawed, and assayed. No decrease in activity was noted.

As is apparent from the above described results, the LK 1 has phsicochemical properties distinguishable from those of known lymphokines such as LT, TNF or IFN. Also, the present monoclonal antibody is novel because it exhibits an immunologically-specific neutralization with the cytotoxic activity of the novel lymphokine LK 1.

EXPERIMENT B-1

Growth inhibition effect on malignant tumors

The growth inhibition effect of LK 1 on several human cells was studies by use of LK 1 preparations obtained by the method described in Experiments A-1 and A-3.

One human cell ($10^6$ cells) listed in Table I was suspended in 1 ml of conventional nutrient medium supplemented with foetal calf serum, cultured for one day, added with 0.1 ml of a physiological saline containing either 50 units or 500 units of the LK 1 preparation, prepared by the method described in Experiment A-1 or A-3, and incubated at 37° C. for two days. After completion of the culture, the viable cell was stained with neutral red, a type of staining agent, according to the method described in *Applied Microbiology*, Vol. 22, No. 4, pp. 671-677 (1971), and the staining agent was eluted by use of an acidified ethanol solution. Thereafter, the number of the viable cell was estimated by measuring the absorbance of the eluate at a wave length of 540 nm.

As control, 0.1 ml of an LK 1 free physiological saline was used.

Growth inhibition (%) was calculated with the following equation:

$$\text{Growth inhibition (\%)} = \left(1 - \frac{\text{Absorbance when } LK \text{ 1 used}}{\text{Absorbance of the control}}\right) \times 100$$

The results are given in Table I.

As is evident from the results in Table I, it was confirmed that LK 1 does not affect substantially normal cells, but inhibits extremely the growth of various malignant tumor cells. Also was confirmed that the effect of a partially-purified LK 1 compares well with that of highly-purified one.

TABLE I

| Name of cell line | Source of cell line | LK 1 at Experiment A-1 50 units | LK 1 at Experiment A-1 500 units | LK 1 at Experiment A-3 50 units | LK 1 at Experiment A-3 500 units |
|---|---|---|---|---|---|
| HEp#2* | Larynx epidermoid carcinoma | 32 | 41 | 48 | 70 |
| PC-8* | Lung carcinoma | 28 | 39 | 57 | 81 |
| MKN 7* | Gastric cancer | 37 | 44 | 61 | 76 |
| HLE* | Liver carcinoma | 31 | 40 | 54 | 72 |
| HeLa* | Cervix epitheloid carcinoma | 26 | 36 | 45 | 69 |
| L-132** | Embryonic lung | 4 | −2 | 1 | −3 |
| Chang liver** | Liver | 2 | −4 | −5 | 1 |
| Giradi heart** | Heart | −3 | 2 | −1 | −3 |

Note:
*indicates human cell lines of malignant tumor origins;
**those of normal origins.

EXPERIEMENT B-2

A group of BALB/c mice were transplanted with Meth A cell of mouse sarcoma origin. From the tenth day after the transplantation, the mice were injected subcutaneously with physiological saline containing an LK 1 preparation, obtained by the method described in Experiment A-3, in a dosage of 100 or 1,000 units/kg daily for 15 days. Thereafter, the mice were sacrificed, and the tumor masses, formed in the animals, were measured.

The results are shown in Table II.

TABLE II

| Treatment | Dosage per day (units/kg) | Tumor mass (g) |
|---|---|---|
| Control | 10 | 5.6 ± 0.7 |
| LK 1 | 100 | 3.4 ± 0.4* |
| | 1,000 | 2.9 ± 0.3* |

Note:
*means the values statistically significant against the control in a level of significance of 5%.

EXPERIMENT B-3

Groups of BALB/c nude mice were transplanted subcutaneously in their dorsum areas with small fragments of human breast cancer tissue.

After the tumor masses grew to about 200 mm³ in the bodies of the animals, physiological saline containing an LK 1 preparation, obtained by the method described in Experiment A-1 or A-3, was injected intravenously once every day in a dosage of either 100 units/kg or 1,000 units/kg for twenty days. Thereafter, the animals were sacrificed, and the resultant tumor masses were weighed.

The results are given in Table III.

TABLE III

| Treatment | Dosage per day (units/kg) | Tumor mass (g) |
|---|---|---|
| Control | 0 | 10.5 ± 1.1 |
| LK 1 at Experiment A-1 | 100 | 7.2 ± 0.8* |
| | 1,000 | 6.9 ± 0.5* |
| LK 1 at Experiment A-3 | 100 | 6.4 ± 0.6* |
| | 1,000 | 5.8 ± 0.7* |

Note:
*means the values statistically significant against the control in a level of significance of 5%.

EXPERIMENT B-4

An acute toxicity test, wherein a group of 20-day old mice were administered with an LK 1 preparation, obtained by the method described in Experiment A-3, confirmed that the toxicity of the preparation was extremely low, i.e. $LD_{50}$, $10^9$ units or more, when injected intraperitoneally.

As is obvious from the above experiments, the LK 1 of the present invention is very effective in the growth inhibition of malignant tumors in vitro as well as in vivo. Furthermore, the administration of the LK 1 is very safe in view that a high dosage does not practically affect normal cells, while low dosage remarkably affects tumor cells.

The effective dosage of the present LK 1 generally falls in the range of 5–500,000,000 units/day for an adult; more particularly, for local administration, e.g. in the form of local injection or collyrium, 5–10,000,000 units/day; for percutaneous or permucosal administration, e.g. in the form of ointment or suppository, 10–50,000,000 units/day; for systemic administration, e.g. intravenous- or intramascular injection, 50–100,000,000 units/day; and oral administration, 500–500,000,000 units/day, but the dosage is freely variable dependent upon its instructions and patient's symptom.

Although the LK 1 may be prepared into medicine in usual way after admixing with suitable conventional carrier, base and/or vehicle, the LK 1 content thereof should be at least 5 units/g in view of its toxicity, effective dosage, and safety.

The shape and form of prophylactic- and/or therapeutic agents for LK 1-sensitive diseases may be freely chosen: for example, for oral administration, it may be shaped into preparations for enteric uses, e.g. capsule, tablet or powder; for rectal administration, suppository; for injection, it may be, for example, prepared into a lyophilized injection which is dissolved, prior to use, into an injection solution with distilled water, as well as in the forms of collunarium, collyrium, or ointment.

In the treatment of a malignant tumor patient, for example, a tumor tissue fragment extracted from the patient may be treated in vitro with the LK 1 to enhance the immunogenicity of the tissue fragment, and administrated to the patient to obtain a much more effective treatment of the malignant tumor.

The following Examples A, B and C illustrate the LK 1 production, pharmaceutical compositions containing LK 1, and the LK 1-specific monoclonal antibody, respectively.

EXAMPLE A-1

A human lymphoblastoid line, BALL-1, was inoculated on Eagle's minimal essential medium (pH 7.4), supplemented with 20% foetal calf serum, and cultured in vitro in suspension at 37° C. in usual way. The proliferated human cell was then washed with serum-free Eagle's minimal essential medium (pH 7.4), and resuspended in a fresh preparation of the same culture medium to give a cell density of about $1\times 10^7$ cells/ml. The cell suspension was added with Sendai virus in an dosage of about 1,000 haemagglutination titers/ml, and incubated at 38° C. for one day to induce LK 1 production. After centrifuging the resultant culture at 4° C. and about $1,000\times g$, the supernatant was dialyzed against physiological saline containing 0.01 M phosphate buffer (pH 7.2) for 15 hours, and treated with a membrane filter. The filtrate was then passed through a column of anti-LK 1 antibody similarly as in Experiment A-1, and the unadsorbed fraction was purified similarly as in Experiment A-3 by means of affinity chromatography using a column of an anti-LK 1 antibody-bound gel, and concentrated to obtain a concentrate having a specific LK 1 activity of about $10^9$ units/mg protein.

The yield was about $2\times 10^6$ units/liter of the induced cell suspension.

EXAMPLE A-2

Newborn hamsters were injected with a conventional antiserum prepared from rabbit to weaken their immunoreaction, transplanted subcutaneously with a human lymphoblastoid line, BALL-1, and fed for three weeks the usual way. The tumor masses, about 15 g each, formed subcutaneously in the animals, were extracted, minced, and disaggregated in physiological saline. After washing with serum-free RPMI 1640 medium (pH 7.2), the proliferated cell was resuspended in a fresh preparation of the same culture medium to give a cell density of about $5\times 10^6$ cells/ml. The cell suspension was added with Sendai virus and *E. coli* endotoxin in respective dosage of about 1,000 haemagglutination titers/ml and about 10 µg/ml, and incubated at 37° C. for one day to induce LK 1 production. After centrifuging the culture at 4° C. and about $1,000\times g$ to remove the sediment, the supernatant was dialyzed against physiological saline containing 0.01 M phosphate buffer (pH 7.2) for 21 hours, and treated with a membrane filter. The filtrate was purified with a column of antibody similarly as in Example A-1, and the eluate solution was concentrated and lyophilized to obtain a powder having a specific LK 1 activity of about $10^9$ units/mg protein.

The yield was about $4.0\times 10^7$ units.

EXAMPLE A-3

Adult nude mice were transplanted intraperitoneally with a human lymphoblastoid line, TALL-1, fed in usual way for five weeks, injected intraperitoneally with Newcastle disease virus (about 3,000 haemagglutination titers per nude mouse) which had been substantially preinactivated with uv-irradiation, and sacrificed 24 hours after the injection, followed by harvest of their ascite fluids. The ascite fluids were purified, concentrated, and lyophilized similarly as in Example A-2 to obtain a powder possessing LK 1 activity.

The yield was about $4.0\times 10^6$ units per nude mouse.

EXAMPLE A-4

Adult mice were irradiated with about 400 rem of x-ray to weaken their immunoreaction, transplanted subcutaneously with a human lymphoblastoid line, Mono-1, and fed in usual for three weeks. The tumor masses, about 10 g each, formed subcutaneously in the animals, were extracted and disaggregated similarly as in Example A-2. The human cell was thus obtained was suspended similarly as in Example A-2, after which the resultant cell suspension was added with Sendai virus and concanavalin A in respective dosage of about 500 haemagglutination titers/ml and 0.8 µg/ml, a and incubated at 37° C. for one day to induce LK 1 production. Thereafter, the culture was purified, concentrated, and lyophilized similarly as in Example A-2 to obtain a powder possessing LK 1 activity.

The yield was about $2.4\times 10^7$ units per mouse.

EXAMPLE A-5

Newborn hamsters were transplanted with a human lymphoblastoid line, Namalwa (ATCC CRL 1432), similarly as in Example A-2, and fed in usual way for four weeks. The tumor masses, about 20 g each, formed subcutaneously in the animals, were extracted and disaggregated to obtain a cell suspension having a cell density of about $3\times 10^6$ cells/ml. The cell suspension was added with Sendai virus in a dosage of about 1,000 haemagglutination titers/ml, and incubated at 36° C. for two days to induce LK 1 production. The culture was purified and concentrated similarly as in Example A-1 to obtain a concentrate possessing LK 1 activity.

The yield was about $2.6\times 10^7$ units per hamster.

EXAMPLE A-6

A human lymphoblastoid line, NALL-1, was suspended in physiological saline, and placed in an about 10 ml cylindrical plastic diffusion chamber equipped with a membrane filter having a nominal pore size of about 0.5 µ. The chamber was embedded intraperitoneally in an adult rat, and the animal was fed in usual way for four weeks. After removal of the chamber, it was found that the cell density in the chamber was about $5\times 10^8$ cells/ml, which was about $10^2$-fold or higher in comparison with the case of proliferating in vitro in a $CO_2$ incubator using a nutrient culture medium. The human cell was suspended in culture medium similarly as in Example A-2, added with Newcastle disease virus (about 500 haemagglutination titers/ml), which had been preinactivated with uv-irradiation, and phytohaemagglutinin (about 50 µg/ml), and incubated at 37° C. for one day to induce LK 1 production. Thereafter, the culture was purified, concentrated, and lyophilized similarly as in Example A-2 to obtain a powder possessing LK 1 activity.

The yield was about $1.0\times 10^7$ units per rat.

EXAMPLE A-7

A human lymphoblastoid line, CCRF-CEM (ATCC CCL 119), was inoculated in the allantoic cavities of embryonated eggs which had been incubated at 37° C. for five days, and the eggs were further incubated at this temperature for an additional one week. The proliferated human cell was harvested from the eggs, and suspended similarly as in Example A-1 to give a cell density of $5\times 10^6$ cells/ml. The cell suspension was then added with Sendai virus (about 500 haemagglutination titers/ml), and incubated at 37° C. for one day to induce LK 1 production. The resultant culture was purified and concentrated similarly as in Example A-2 to obtain a powder possessing LK 1 activity.

The yield was about $8.0\times 10^5$ units per ten embryonated eggs.

EXAMPLE B-1

Injection

Five hundred thousand units of the LK 1 specimen, prepared in Example A-2, was dissolved in 200 ml physiological saline, and filtered under sterile conditions by use of a membrane filter. Two ml aliquots of the filtrate was distributed into sterized glass vials, lyophilized, and sealed to obtain a powdered injection.

This injection is favorably usable for treating breast cancer, lung carcinoma, liver carcinoma, and leukaemia.

EXAMPLE B-2

Ointment

The LK 1 specimen, prepared in Example A-3, was kneaded with a minimal amount of liquid paraffin to homogeneity. The mixture was then added with white petrolatum in usual way to obtain an ointment having an LK 1 content of 20,000 units/g.

This ointment is favorably usable for treating skin carcinoma, breast cancer, and lumphoma.

EXAMPLE B-3

Collyrium

A mixture of 800 ml distilled water, 5 ml β-phenylethyl alcohol and 20,000,000 units of the LK 1 specimen, prepared in Example A-4, was admixed with sodium chloride in an additional amount of distilled water to obtain 1,000 ml of an isotonic solution.

The solution is favorably usable as collyrium for treating retinoblastoma.

EXAMPLE B-4

Enteric coated tablet

Enteric coated tablets were prepared according to conventional method by tabletting a mixture of starch, maltose, and an LK 1 specimen prepared in Example A-7 to give an LK 1 content of 200,000 units per tablet (100 mg), followed by coating the tablets with phthalate ester of methyl cellulose.

The tablets are favorably usable for treating colon carcinoma, and liver carcinoma.

EXAMPLE C-1

Mice were immunized similarly as in Experiment A-2, except that a high-purity LK 1 obtained by the method described in Experiment A-1 was used as the antigen. Thereafter, the spleen cell of the animals was suspended together with a mouse myeloma line, P3-NS-1/1-Ag4-1, a product of Dainippon Pharmaceutical Co., Ltd., Osaka, Japan, in a salt solution containing 140 mM NaCl, 54 mM KCl, 1 mM NaH$_2$PO$_4$, and 2 mM CaCl$_2$ to give respective cell density of $10^4$ cells/ml. To the cell suspension was added a fresh salt solution of the same composition but containing, in addition, Sendai virus, which had been inactivated with uv-irradiation, under icechilled conditions, and the mixture was allowed to stand for five minutes. Thereafter, the mixture was diluted about 20-times in 37° C. RPMI 1640 medium, and the hybridoma cell capable of producing anti-LK 1 antibody were cloned similarly as in Experiment A-2. The cloned hybridoma cell was transplanted intraperioneally into 7-day old hamsters (about $10^7$ cells per hamster) whose immunoreaction had been weakened with conventional procedure, and the monoclonal antibody was recovered from the bodies of the animals similarly as in Experiment A-2.

Like the monoclonal antibody prepared in Experiment A-2, the product exhibited an immunologically-specific neutralization with the cytotoxic activity of LK 1.

The stability of the monoclonal antibody in aqueous solution was studied by assaying the residual neutralizing activities after incubating under prescribed conditions: On incubation at pH 7.2 and different temperatures for 30 minutes, 80% or more of the activity was retained at 60° C., but 90% or more was lost at 70° C. After incubation at 4° C. and different pH levels for 16 hours, the activity was stable in the pH range of 2.0–11.0.

On studying several properties of the monoclonal antibody, it was found that the present monoclonal antibody was resistant to 2-mercaptoethanol, and effects a specific antigen-antibody reaction with anti-mouse immunoglobulin G antibody. Thus, the present monoclonal antibody is grouped into the class immunoglobulin antibody.

EXAMPLE C-2

A monoclonal anti-LK 1 antibody was prepared similarly as in Example C-1, except that a mouse myeloma line, SP2/0-Ag14, available from Dainippon Pharmaceutical Co., Ltd., Osaka, Japan, was replaced for P3-NS-1/1-Ag4-1.

On studying the immunologically-specific neutralization by the monoclonal antibody with the cytotoxic activity of LK 1, a similar result as in Example C-1 was obtained. Thus, the monoclonal antibody is also grouped into the class of immunoglobulin G antibody.

While the invention has been particularly shown and described with reference to preferred embodiments thereof, it will be understood by those skilled in the art that the foregoing and other changes can be made therein without departing from the spirit and scope of the invention.

We claim:

1. A lumphokine (LK 1), which has the following physicochemical properties:
   (a) Molecular weight;
      20,000±2,000 daltons
   (b) Isoelectric point;
      pI=5.6±0.2
   (c) Electrophoretic mobility;
      on Disc-PAGE, Rf=0.29±0.02
   (d) uv-Absorption spectrum;
      an absorption maximum at a neighborhood of 280 nm
   (e) Solubility in solvents;
      soluble in water, physiological saline and phosphate buffer
      scarcely soluble or insoluble in ethyl ether, ethyl acetate or chloroform
   (f) Coloring reaction;
      protein-positive by the Lowry's method or microburet method
      sugar-positive by the phenol-sulfuric acid method or anthrone-sulfuric acid method
   (g) Biological activities;
      cytotoxic on L 929 cell
      growth-inhibitive on KB cell
      substantially free from interferon activity
   (h) Stability in aqueous solution;

stable up to 60° C. when incubated at pH 7.2 for 30 minutes stable in the pH range of 4.0-11.0 when incubated at 4° C. for 16 hours, and (i) Stability on cryopreservation;

stable at −10° C. over a period of one month or longer.

2. LK 1 produced by a method which comprises the steps of:

proliferating a human cell capable of producing LK 1;

exposing a proliferated human cell to an LK 1 inducer under the conditions to accumulate a substantial amount of LK 1; and recovering the accumulated LK 1.

3. A pharmaceutical composition, comprising a pharmaceutically-acceptable carrier and an amount of LK 1 effective to signficantly inhibit the growth of tumor cells.

4. The composition as set forth in claim 3, which contains LK 1 in an amount of at least 5 units/g of said composition.

5. The composition as set forth in claim 3, wherein said composition is an injection, collyrium, ointment, suppository, or collunarium.

6. A substantially-pure LK 1.

7. The LK 1 as set forth in claim 6, whose specific activity is at least $10^6$ units/mg protein.

* * * * *

UNITED STATES PATENT AND TRADEMARK OFFICE
CERTIFICATE OF CORRECTION

PATENT NO.  : 4,758,549
DATED       : July 19, 1988
INVENTOR(S) : MITSUHASHI et al It is certified that error appears in the above-identified patent and that said Letters Patent is hereby corrected as shown below:

[73]  Assignee:  Change "Mayashibara" to read --Hayashibara--
[30]  Foreign Application Priority Data:  Change the second priority application number to --58-244598--;
Column 1, line 2:   change "their" to read --its--;
          line 34:  change "lumphokines" to read --lymphokines--;
          line 39:  change "lumphokines" to read --lymphokines--;
          line 40:  change "lum-" to read --lym- --;
Column 2, line 15:  change "lumphocyte" to read --lymphocite--;
          line 17:  change "lumphocyte" to read --lymphocite--;
          line 29:  change "tiltered" to read --titered--;
          line 65:  change "circino-" to read --carcino- --;
Column 3, line 10:  change "lumphocite" to read --lymphocite--;
Column 4, line 19:  change "increse" to read --increases--;
Column 6, line 67:  change "charmatography" to read --chromatography--;
Column 7, line 1:   change "afinnity" to read --affinity--;
          line 32:  change "maemagglutination" to read --haemagglutination--;
          line 64:  change "lyopilized" to read --lyophilized--;
Column 9, line 15:  change "were" to read --was--;

UNITED STATES PATENT AND TRADEMARK OFFICE
CERTIFICATE OF CORRECTION

PATENT NO. : 4,758,549

DATED : July 19, 1988

INVENTOR(S) : MITSUHASHI et al

It is certified that error appears in the above-identified patent and that said Letters Patent is hereby corrected as shown below:

Column 10, line 22: change "phsicochemical" to read --physio-chemical--;

Column 15, line 23: change "lumphoma" to read --lymphoma--;

Column 16, line 21: add --of-- after "class";

line 22: add --G-- before "antibody";

line 43: change "lumphokine" to read --lymphokine--.

Signed and Sealed this

Twenty-third Day of May, 1989

Attest:

DONALD J. QUIGG

*Attesting Officer*　　　*Commissioner of Patents and Trademarks*